(12) United States Patent
Okada (10) Patent No.: US 7,496,219 B2
(45) Date of Patent: Feb. 24, 2009

(54) THERMAL DEVELOPMENT APPARATUS

(75) Inventor: Koichi Okada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 514 days.

(21) Appl. No.: 11/214,757

(22) Filed: Aug. 31, 2005

(65) Prior Publication Data
US 2006/0050137 A1 Mar. 9, 2006

(30) Foreign Application Priority Data
Sep. 8, 2004 (JP) ............... P.2004-260947

(51) Int. Cl.
*G06K 9/00* (2006.01)
(52) U.S. Cl. .................................................... 382/128
(58) Field of Classification Search ............... 382/128, 382/131, 132, 151, 294, 296; 378/37
See application file for complete search history.

(56) References Cited

U.S. PATENT DOCUMENTS

| | | | | |
|---|---|---|---|---|
| 5,999,842 A | * | 12/1999 | Harrison et al. | 600/474 |
| 6,198,799 B1 | * | 3/2001 | Ono et al. | 378/98.2 |
| 6,891,557 B2 | * | 5/2005 | Sumi et al. | 347/228 |
| 7,155,048 B2 | * | 12/2006 | Ohara | 382/132 |
| 2005/0008262 A1 | * | 1/2005 | Komiya et al. | 382/305 |
| 2005/0111721 A1 | * | 5/2005 | Bamberger et al. | 382/132 |

FOREIGN PATENT DOCUMENTS

JP 2004-135856 A 5/2004

* cited by examiner

*Primary Examiner*—Daniel G Mariam
(74) *Attorney, Agent, or Firm*—Sughrue Mion, PLLC (57) ABSTRACT

An image processing section is disposed in a thermal development apparatus. The image processing section implements a 180-degree rotation process on one of right and left mammo image data supplied from a CR apparatus. An exposing section implements an exposing process based on the mammo image data after an image process.

15 Claims, 5 Drawing Sheets

THERMAL DEVELOPMENT APPARATUS

This application is based on Japanese Patent application JP 2004-260947, filed Sep. 8, 2004, the entire content of which is hereby incorporated by reference. This claim for priority benefit is being filed concurrently with the filing of this application.

BACKGROUND OF THE INVENTION

1. Technical Field of the Invention

The present invention relates to a thermal development apparatus which has a transporting section that transports a thermal development recording material, and an exposing section that exposes the thermal development recording material to form a latent image, and which heats the thermal development recording material after exposure to make the latent image visible.

2. Description of the Related Art

Mammography is an imaging technique which forms right and left breast images of a woman (hereinafter, such breast images are referred to as mammo images) for breast cancer screening or the like. Mammo images based on right and left mammo image data are finally made visible, and subjected to comparative observation by the doctor. In this observation, it is important to discern a slight difference between the images. Therefore, a mammo image is requested to have a high sharpness and a high resolution.

Recently, a medical system has been developed in which a radiographic imaging apparatus such as a CR apparatus is connected to a thermal development apparatus via a network, and mammo image data are supplied online from the radiographic imaging apparatus to the thermal development apparatus to develop a mammo image.

Here, the developed right and left mammo images are subjected to a diagnosis by the doctor in a mode where chest wall portions are butted against each other (i.e., in a mode where the right and left beasts are placed axisymmetrically).

The doctor comparatively observes the right and left mammo images which are hung on a schaukasten, and makes a diagnosis while discerning a slight difference between the images in shape and density. However, the diagnosis is based on the observation conducted with the naked human eye. In consideration of this, photographs of the right and left mammo images ought to be those which are formed so as not to cause visual unbalance. For example, the lengths of margins in the peripheries of the photographs are to be equal to each other.

As a related art technique for forming a photograph of right and left mammo images in which visual balance is considered, for example, an X-ray image forming method is disclosed in JP-A-2004-135856 (hereafter "JPA '856"). In the X-ray image forming method disclosed in JPA '856, when right and left mammo images are to be visualized on a single film, their layout positions are finely adjusted so as not to form margins, and the right and left breasts on the film are placed back to back in a manner where the chest walls overlap with each other, thereby obtaining an easy-to-read mammo image.

As described above, when mammo images are to be developed, a technique for reducing visual unbalance between right and left mammo images is necessary. From this point of view, the present inventor has variously studied current medical systems to clarify points to be improved. As a result, the following two items (first and second points to be improved) are clarified. Hereinafter, the study result will be described with reference to the drawings.

(First Point to be Improved)

FIGS. 4A to 4D are diagrams illustrating one of the points to be improved (dispersion of margins) in mammo image formation in the current mammography.

Figure 4A:
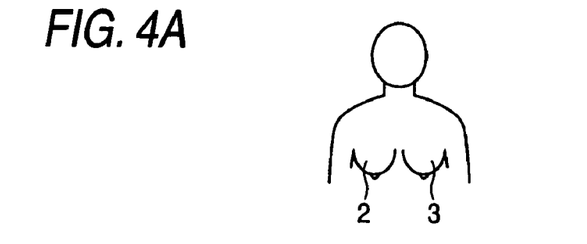
FIGS. 4A to 4D are diagrams illustrating dispersion of margins in mammo image formation in a related art mammography.

As shown in FIG. 4A, the underarm sides of the right and left breasts 2, 3 of a woman to be examined are "the outer sides (in the figure, indicated by thick lines)". In discussion of a rotation process or the like of a photograph image, a reference of some sort is required in viewing of a photograph. Hereinafter, the reference is provided by indicating the outer side of a breast with a thick line. In the drawings attached to the specification, a mammo image data is illustrated as an image.

Figure 4B:
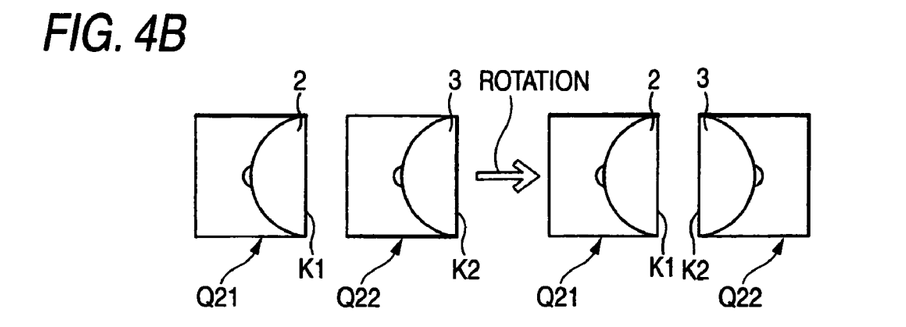

As shown in the left side of FIG. 4B, a CR apparatus obtains mammo image data Q21, Q22 which are produced by photographing the right and left breasts 2, 3. The mammo image data Q21 is obtained by photographing the right breast 2, and the mammo image data Q22 by photographing the left breast 3. In the figures, K1 and K2 denote the chest wall. Usually, a CR apparatus conducts a process of rotating the right or left (in this example, left) mammo image data Q22 by 180 degrees as shown in the right side of FIG. 4B, and thereafter transmits the mammo image data Q21, Q22 to a thermal development apparatus.

Figure 4C:
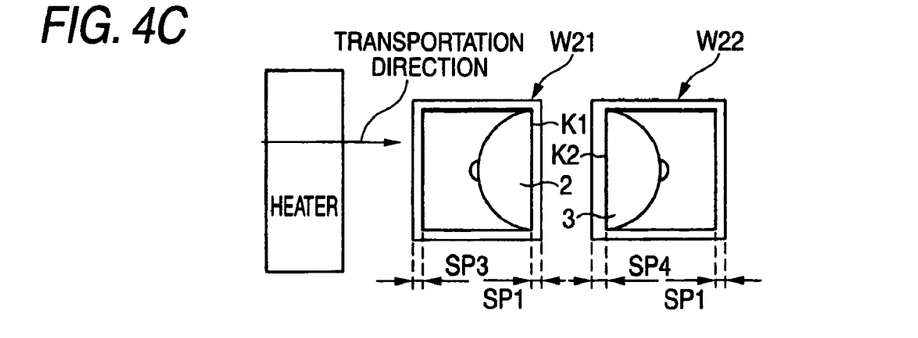

In the thermal development apparatus, a laser exposing process is applied to a thermal development recording material to form a latent image of a mammo image, and the latent image is made visual by thermal development. In the heat developing step, as shown in FIG. 4C, for example, a roll film of a thermal development recording material is transported in the direction of the arrow, a heating process is conducted by a heater disposed below a transporting path, and a process of cutting the rear end of the thermal development recording material film on which the visible image is formed is conducted. As a result of these processes, a photograph W21 or W22 on which the visible image is formed.

Figure 4D:
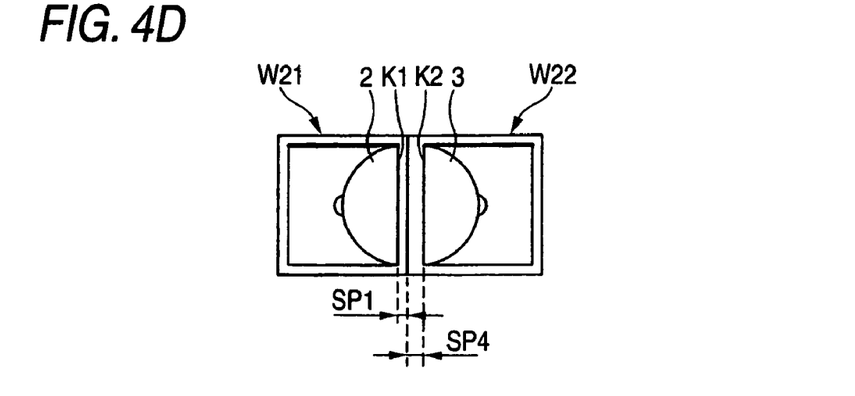

The lengths of margins (SP1) formed in tip end portions of the photographs W21, W22 are equal to each other because of the following reason. In the laser exposing process, the laser exposure is started after the elapse of a predetermined time period from detection of the tip end of the transported thermal development recording material film. The tip end can be accurately detected, and hence the margin amount at the tip end can be controlled fairly accurately. By contrast, margins (SP3, SP4) at the rear ends are dispersed because the cutting positions of the thermal development recording material film are varied. In the case where the margins in the rear end portions of the right and left photographs (W21, W22) are dispersed, when the chest wall portions of the right and left photographs are butted against each other, the margins of the butted portions of the photographs W21, W22 are dispersed (one of the portions: SP1, and the other portion: SP4) as shown in FIG. 4D. Therefore, a visual impression is so unbalanced that the doctor hardly makes a diagnosis.

The CR apparatus rotates the mammo image data of the left breast 3 by 180 degrees, thereby allowing the two photographs to be discharged to a discharge tray of the thermal development apparatus in a state where the directions of the outer sides coincide with each other as shown in FIG. 4C. Since the directions of the outer sides coincide with each other, the doctor is requested only to fix the outer sides of the two photographs to a schaukasten, in order to produce a state where the chest walls are opposed to each other. When the rotation process is not conducted, the doctor must fix the photograph of the left breast 3 discharged from the thermal development apparatus, to the schaukasten after manually rotating the photograph by 180 degrees. This operation is cumbersome. In a CR apparatus, in order to enable the doctor to efficiently make a diagnosis, a process of rotating one of right and left mammo image data by 180 degrees is usually conducted as described above.

(Second Point to be Improved)

The second point to be improved is uneven density due to the temperature distribution of the heater. FIGS. 5A to 5G are diagrams illustrating the other of the points to be improved (occurrence of uneven density) in mammo image formation in the current mammography.

Figure 5A:
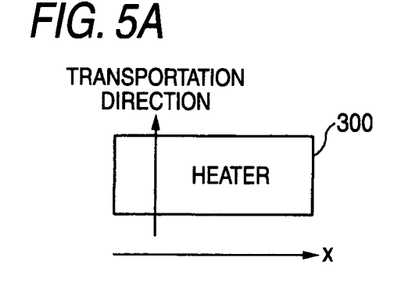
FIGS. 5A to 5G are diagrams illustrating occurrence of uneven density in mammo image formation in the related art mammography.
Figure 5B:
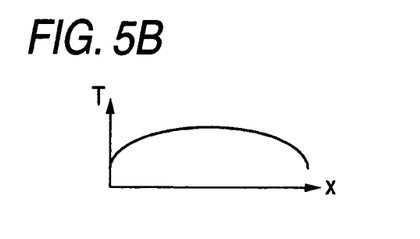
Figure 5C:
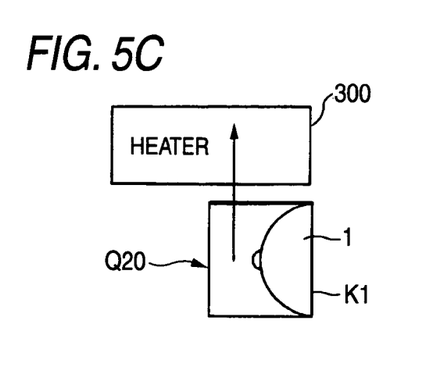
Figure 5D:
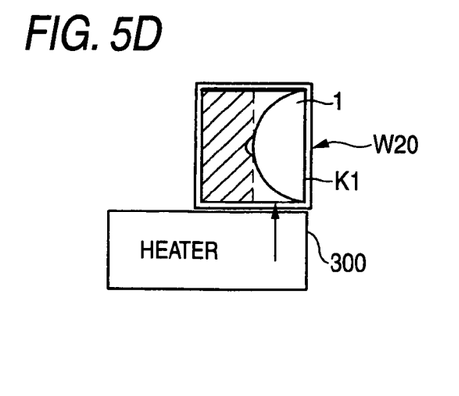

FIG. 5A shows a heater 300 used in thermal development of a thermal development apparatus. The temperature distribution of the heater in the direction x which is perpendicular to a transportation direction of a thermal development recording material is not uniform as shown in, for example, FIG. 5B. When a latent image 1 of a breast is formed in a mode where the chest wall K1 is parallel to the transportation direction as shown in FIG. 5C, uneven density occurs in a photograph W20 after thermal development as shown in FIG. 5D, because the temperature of a middle portion of the heater 300 is high. In FIG. 5D, a high density portion is hatched (this is applicable also to the subsequent figures).

Figure 5E:
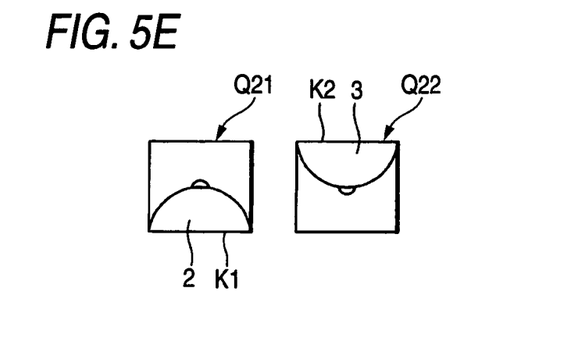
Figure 5F:
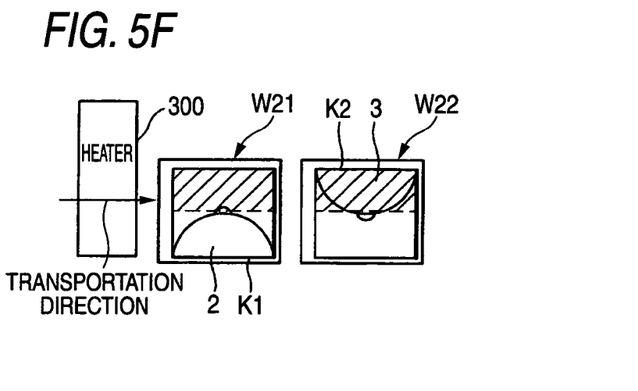
Figure 5G:
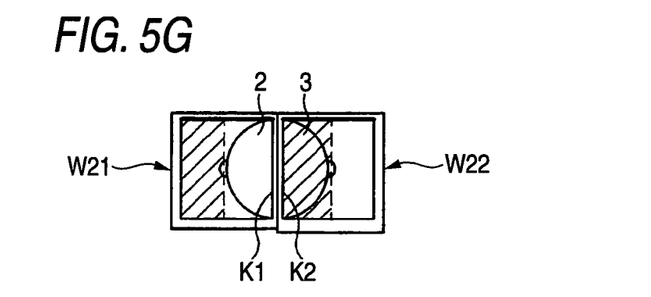

Actually, mammo image data Q21, Q22 which are output from the CR apparatus, and which are as shown in FIG. 5E are subjected to the thermal development. Breast latent images 2, 3 are formed on the basis of the mammo image data Q21, Q22 in a mode where the chest walls K1, K2 are parallel to the transportation direction as shown in FIG. 5F, and then thermal development is implemented. As a result, uneven density occurs in the photographs W21, W22 after the development. Thereafter, the photographs W21, W22 of the right and left breasts are fixed to a schaukasten in such a manner that the chest walls K1, K2 are opposed to each other as shown in FIG. 5G. In the resulting photographs, the density relationships in the right and left mammo images are opposite to each other, and an unbalanced visual impression is produced. Therefore, the doctor hardly makes a diagnosis.

SUMMARY OF THE INVENTION

The invention has been conducted under the above-mentioned circumstances. It is an object of the invention to provide a thermal development apparatus that can produce right and left breast images in which consideration is made so as not to produce visual unbalance, and which is suitable to a diagnosis by a doctor.

The thermal development apparatus of the invention is an apparatus which has a transporting section that transports a thermal development recording material, and an exposing section that exposes the thermal development recording material to form a latent image, the apparatus heating the thermal development recording material after exposure to make the latent image visible, wherein the thermal development apparatus comprises image processing section for applying a 180-degree rotation process on one of right and left breast image data which are obtained by mammography and to be supplied to the exposing section, each of right and left images being formed on a sheet of the thermal development recording material.

According to the configuration, it is possible to produce right and left mammo images in which consideration is made so as not to produce visual unbalance, and which is suitable to a diagnosis by a doctor.

In the thermal development apparatus of the invention, when right and left breast images based on the right and left breast image data are to be formed in the thermal development recording material so that chest wall portions of the right and left breast images extend along an end portion which is in a direction perpendicular to a transportation direction of the thermal development recording material, the image processing section preferably applies the rotation process so that each of the chest wall portions of the right and left breast images is formed at a record start position of the thermal development recording material.

According to the configuration, each of the chest wall portions of the right and left breast images is always recorded at the record start position of the thermal development recording material. The margin extending from the tip end of the thermal development recording material to the record start position is always constant. In a state where the chest wall portions of the developed right and left breast images are butted against each other, therefore, the margins in the butted portions are identical with each other. Consequently, the right and left breast images are easily compared with each other.

In the thermal development apparatus of the invention, when right and left breast images based on the right and left breast image data are to be formed in the thermal development recording material so that chest wall portions of the right and left breast images extend along an end portion which is parallel to a transportation direction of the thermal development recording material, the image processing section preferably applies the rotation process so that the right and left breast images are formed so as to be directed in a same direction on the thermal development recording material.

According to the configuration, recording is conducted while the chest wall portions of the right and left breast images are always directed in the same direction. Consequently, positions where uneven density of a breast image caused by temperature unevenness in the thermal development occurs can be made identical with each other in the right and left breast images. Therefore, the developed right and left breast images are easily compared with each other in a state where the chest wall portions of the right and left breast images are butted against each other.

According to the invention, it is possible to provide a thermal development apparatus that can produce right and left breast images in which consideration is made so as not to produce visual unbalance, and which is suitable to a diagnosis by a doctor.

DETAILED DESCRIPTION OF THE INVENTION

Hereinafter, embodiments of the invention will be described with reference to the accompanying drawings.

First Embodiment

Figure 1:
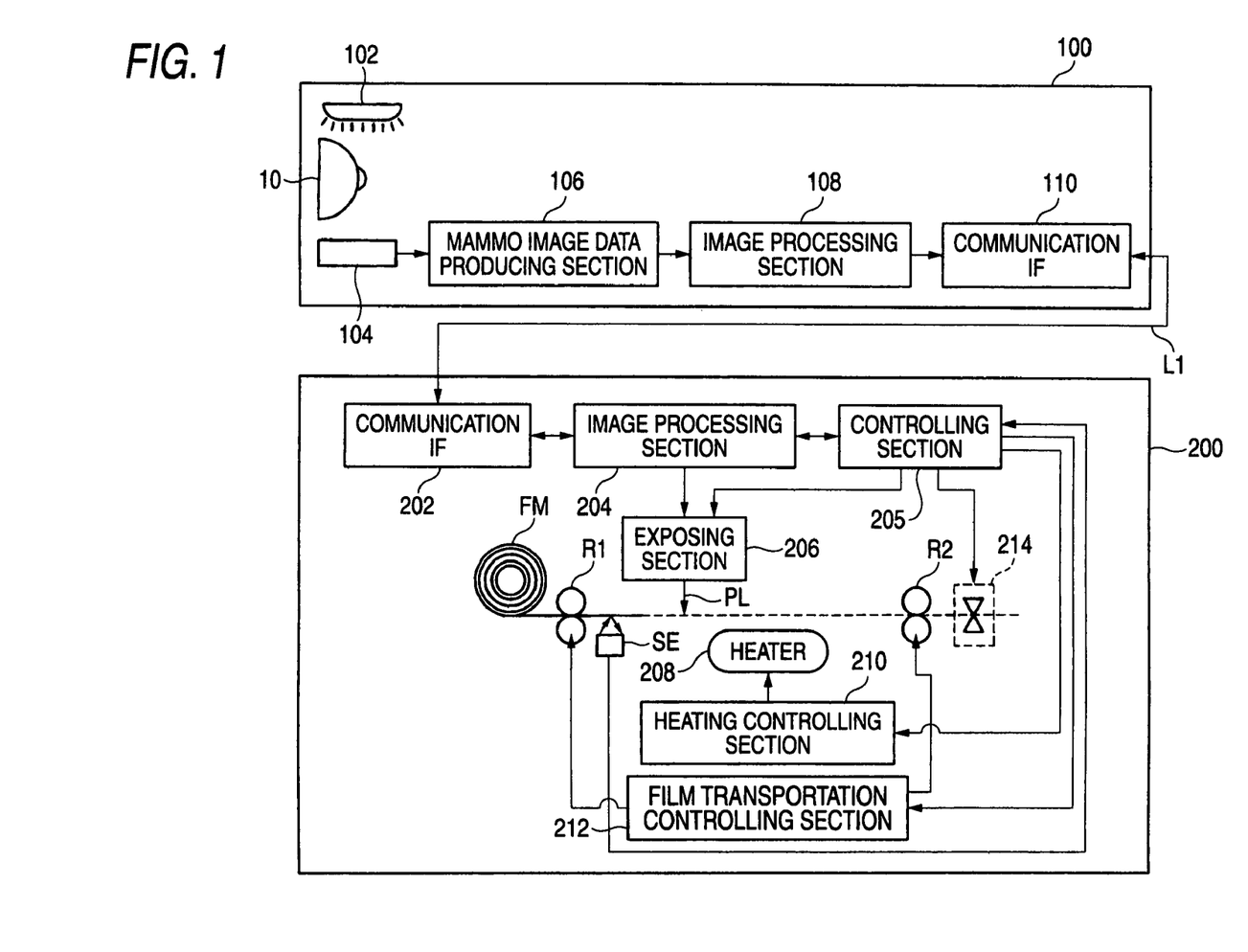
FIG. 1 is a block diagram schematically showing the configuration of a medical system which illustrates a first embodiment of the invention.

FIG. 1 is a block diagram schematically showing the configuration of a medical system which illustrates a first embodiment of the invention.

The medical system shown in FIG. 1 comprises a CR apparatus 100 and a thermal development apparatus 200. The apparatuses are connected to each other via a communication line L1, so that mammo image data are supplied online from the CR apparatus 100 to the thermal development apparatus 200.

The CR apparatus 100 has: an X-ray source 102; X-ray acquisition unit 104 which is configured by a photostimulable phosphor sheet, a flat panel detector, or the like; a mammo image data producing section 106 which converts an image obtained from the X-ray acquisition unit 104 to a mammo image data; an image processing section 108 which applies an image process such as 180-degree rotation on the produced mammo image data; and a communication interface (IF) 110.

In the CR apparatus 100, the breasts 10 of the subject are irradiated with X-rays from the X-ray source 102, the transmitted rays are acquired by the X-ray acquisition unit 104, and the acquired rays are converted to mammo image data by the mammo image data producing section 106. In the image processing section 108, then, a process of rotating one of the right and left mammo image data by 180 degrees is implemented. Thereafter, the right and left mammo image data are transmitted to the thermal development apparatus 200 via the communication IF 110.

The thermal development apparatus 200 conducts laser exposure on a thermal development recording material film FM (in the embodiment, a roll film is used) to form a latent image, on the basis of the mammo image data supplied from the CR apparatus 100, visualizes the latent image by means of thermal development, cuts the film into a predetermined size, and discharges the cut film to a tray.

As the thermal development recording material, a thermal development photosensitive material or a photo/heat-sensitive recording material may be used. A thermal development photosensitive material is a recording material in which an image is recorded (exposed) by a light beam (e.g., a laser beam), and then thermal development is applied to develop a color. A photo/heat-sensitive recording material is a recording material in which an image is recorded by a light beam, and then thermal development is applied to develop a color, or a heat mode (heat) of a laser beam is applied to record an image and at the same time develop a color, and thereafter the image is fixed by light illumination.

As shown in FIG. 1, the thermal development apparatus 200 has: a communication IF 202; an image processing section 204; a controlling section 205 which controls collectively the operations of the sections; an exposing section 206 in which a laser beam PL the intensity of which is modulated on the basis of the mammo image data is scanned by a polygon mirror to form a latent image due to the laser beam on the thermal development recording material film FM; a heater 208 for a thermal development process; a heating controlling section 210 which controls the heating operation of the heater 208; a film transportation controlling section 212 which controls the transportation of the thermal development recording material film FM; a film cutting section 214; a pair of film transportation rollers R1, R2; and a tip end detection sensor SE which detects the tip end of the film.

The image processing section 204 can output the right and left mammo image data supplied from the CR apparatus 100, to the exposing section 206, and apply a 180-degree rotation process on one of the right and left mammo image data to be output to the exposing section 206.

The film transportation controlling section 212 controls the rotation of the film transportation rollers R1, R2 to transport the thermal development recording material film FM from the left side of FIG. 1 in the rightward direction. The tip end detection sensor SE detects that the tip end of the thermal development recording material film FM reaches a predetermined position, and sends a detection signal to the controlling section 205. After the elapse of a predetermined time period from the reception of the signal, the controlling section 205 instructs the exposing section 206 to start the exposure. In response to the instructions for starting exposure, the exposing section 206 implements the laser exposure based on the mammo image data supplied from the image processing section 204 (i.e., irradiation with the laser beam PL to the thermal development recording material film FM), and forms a latent image of the mammo image with starting from the recording start position on the thermal development recording material film FM. The thermal development recording material film FM passes over the heater 208 to be subjected to the thermal development process, whereby the latent image is visualized. The thermal development recording material film FM on which the visible image is formed is cut at the rear end by the film cutting section 214, and then discharged as a photograph of a predetermined size to the tray. In the embodiment, a roll film is used and the roll film on which the visible image is formed is cut by the film cutting section 214, however, a film may be used which is previously cut in a predetermined size. In this case, the thermal development apparatus may not be provided with a film cutting section.

Next, the contents of the image processing of the image processing section 204 mounted on the thermal development apparatus 200 of FIG. 1 will be described.

Figure 2:
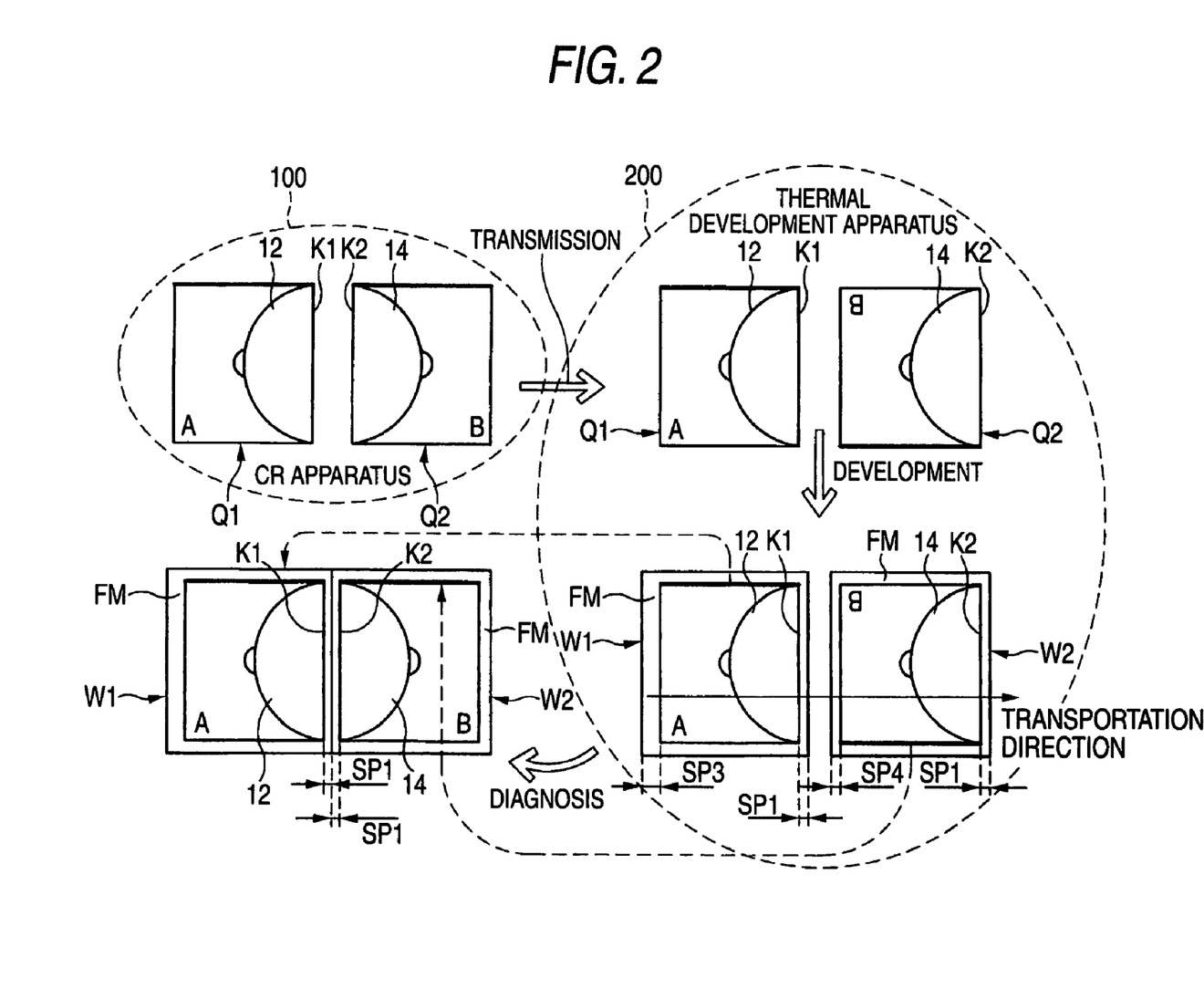
FIG. 2 is a diagram illustrating the contents of image processing implemented inside a thermal development apparatus of the medical system which illustrates the first embodiment of the invention.

FIG. 2 is a diagram illustrating the contents of the image processing implemented inside the thermal development apparatus shown FIG. 1.

As shown in the upper left side of FIG. 2, mammo image data Q1, Q2 in which the directions of the breasts 12, 14 are different from each other are produced in the CR apparatus 100. In the figure, K1 and K2 denote the chest wall portion. The mammo image data Q1, Q2 contain character data "A", "B", respectively. The mammo image data Q1, Q2 are transmitted to the thermal development apparatus 200. The mammo image data Q1 is obtained by photographing the right breast, and the mammo image data Q2 by photographing the left breast. In the embodiment, it is assumed to employ a mode where, when the mammo images based on the mammo image data Q1, Q2 output from the CR apparatus 100 are to recorded on the thermal development recording material film FM, the exposing section 206 records each of the chest wall portions K1, K2 of the mammo image data Q1, Q2 along an end portion of the thermal development recording material film FM which is perpendicular to the transportation direction. This mode shows the operation in the case where the thermal development recording material film FM after the cutting process has a large size (for example, B4 or a quarter size).

As shown in the upper right side of FIG. 2, in the thermal development apparatus 200, the image processing section 204 applies the rotation process on one of the right and left mammo image data Q1, Q2 received from the CR apparatus 100 so that each of the chest wall portions K1, K2 of the right and left mammo image data Q1, Q2 is recorded at the record start position of the thermal development recording material film FM. In the embodiment of FIG. 2, the image processing section 204 rotates the mammo image data Q2 by 180 degrees. Then, the image processing section 204 outputs the mammo image data Q1, Q2 shown in the upper right side of FIG. 2, to the exposing section 206. The exposing section 206 forms a latent image by means of laser exposure on the basis of the mammo image data Q1, Q2 shown in the upper right side of FIG. 2. In the next step or a developing step, as shown in the lower right side of FIG. 2, the thermal development recording material film FM is transported in the transportation direction (from the left side of FIG. 2 to the right side). As a result of the developing step, as shown in the lower right side of FIG. 2, photographs W1, W2 on which the right and left mammo image are respectively developed are discharged to the tray.

Here, it should be noted that the chest walls K1, K2 of the right and left mammo image are perpendicular to the transportation direction, and also that both the chest walls K1, K2 are positioned at the record start positions of the thermal development recording material film FM, respectively. As described above, in the exposing step, the timing period from detection of the tip end of the thermal development recording material film FM by the sensor SE to the start of the exposure is accurately controlled. In a state where the right and left breast photographs W1, W2 discharged to the tray are hung on a schaukasten so that their chest walls are opposed to each other (the lower left side of FIG. 2), both the margins extending from the chest wall portions K1, K2 of the images of the right and left breasts 12, 14 to the end of the thermal development recording material film FM have the size SP1. Therefore, the right and left images are well balanced, and there is no inconvenience of a diagnosis by the doctor.

As described above, in the mode where each of the chest wall portions K1, K2 of the breasts 12, 14 is recorded along the end portion of the thermal development recording material film FM which is in the direction perpendicular to the transportation direction, the image processing section 204 conducts the rotation process so that each of the chest wall portions K1, K2 of the mammo images based on right and left mammo image data Q1, Q2 is at the record start position of the thermal development recording material film FM. Even in the state where the chest wall portions K1, K2 of the developed photographs are butted against each other, therefore, the right and left mammo images can be easily compared with each other.

Second Embodiment

In the first embodiment, the mode where each of the chest wall portions K1, K2 of the breasts 12, 14 is recorded along the end portion of the thermal development recording material film FM which is in the direction perpendicular to the transportation direction has been described. In the embodiment, a mode where each of the chest wall portions K1, K2 of the breasts 12, 14 is recorded along the end portion of the thermal development recording material film FM which is parallel to the transportation direction will be described. This mode shows the operation in the case where the thermal development recording material film FM after the cutting process has a small size (for example, a one-sixth size).

Figure 3:
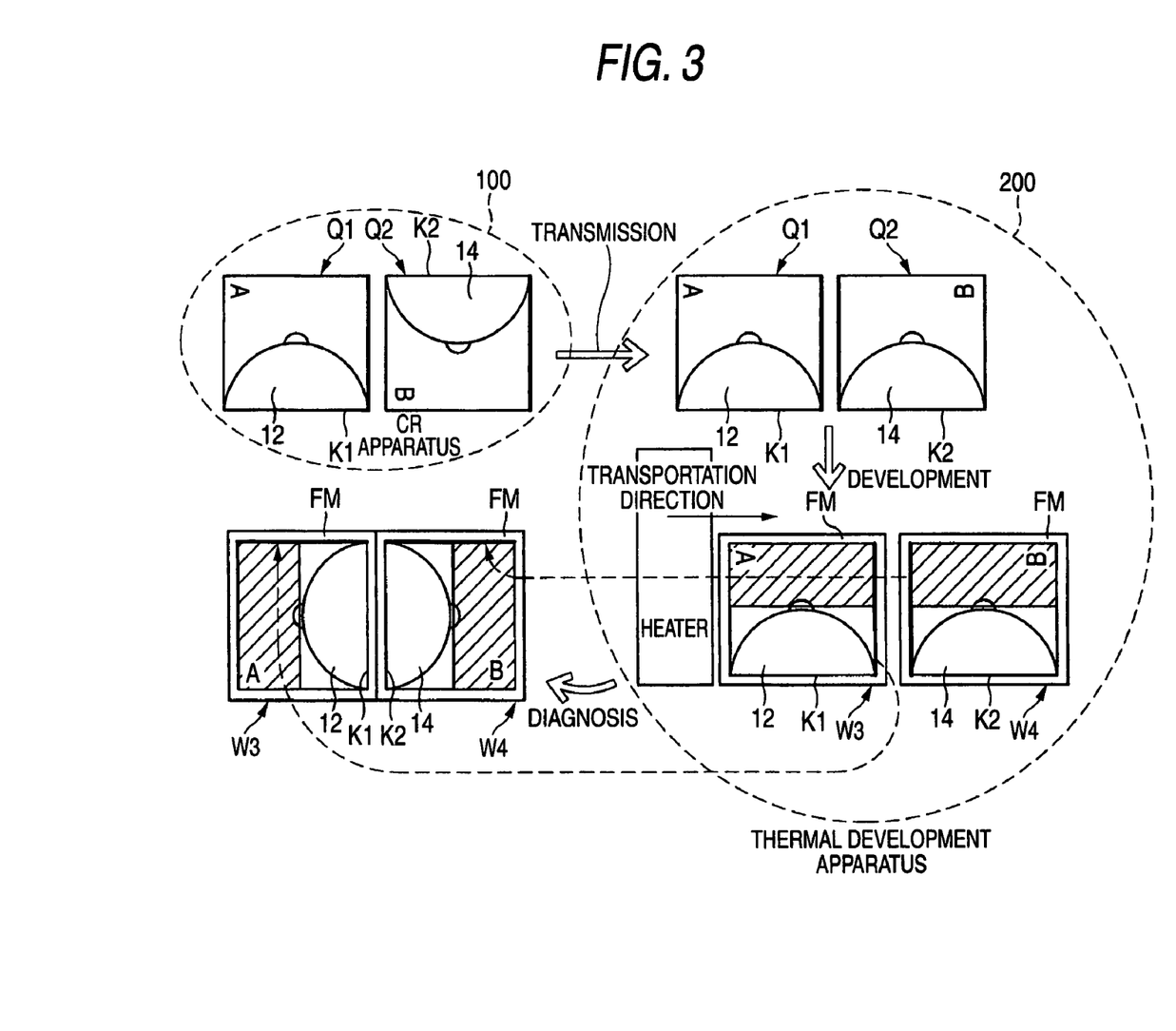
FIG. 3 is a diagram illustrating the contents of image processing implemented inside a thermal development apparatus of a medical system which illustrates a second embodiment of the invention.

FIG. 3 is a diagram illustrating the contents of the image processing implemented inside the thermal development apparatus shown FIG. 1 in the second embodiment.

As shown in the upper left side of FIG. 3, mammo image data Q1, Q2 in which the directions of the breasts 12, 14 are different from each other are produced in the CR apparatus 100. In the figure, K1 and K2 denote the chest wall portion. The mammo image data Q1, Q2 contain character data "A", "B", respectively. The mammo image data Q1, Q2 are transmitted to the thermal development apparatus 200. The mammo image data Q1 is obtained by photographing the right breast, and the mammo image data Q2 by photographing the left breast. In the embodiment, it is assumed to employ a mode where, when the mammo images based on the mammo image data Q1, Q2 output from the CR apparatus 100 are to recorded on the thermal development recording material film FM, the exposing section 206 records each of the chest wall portions K1, K2 of the mammo image data Q1, Q2 along an end portion of the thermal development recording material film FM which is parallel to the transportation direction.

As shown in the upper right side of FIG. 3, in the thermal development apparatus 200, the image processing section 204 applies the rotation process on one of the right and left mammo image data Q1, Q2 received from the CR apparatus 100 so that the chest wall portions K1, K2 of the right and left mammo image data Q1, Q2 are recorded with being directed in the same direction. In the embodiment of FIG. 3, the image processing section 204 rotates the mammo image data Q2 by 180 degrees. Then, the image processing section 204 outputs the mammo image data Q1, Q2 shown in the upper right side of FIG. 3, to the exposing section 206. The exposing section 206 forms a latent image by means of laser exposure on the basis of the mammo image data Q1, Q2 shown in the upper right side of FIG. 3. In the next step or a developing step, as shown in the lower right side of FIG. 3, the thermal development recording material film FM is transported in the direction of the arrow in the figure (from the left side of the sheet face to the right side).

Here, it should be noted that the chest walls K1, K2 of the right and left mammo image are parallel to the transportation direction, and also that both the breasts 12, 14 are directed in the same direction on the thermal development recording material film FM. In a state where the right and left breast photographs W3, W4 discharged to the tray are hung on a schaukasten so that their chest walls are opposed to each other (the lower left side of FIG. 3), the doctor observes a difference between the right and left breasts to make a diagnosis. As shown in the lower right side of FIG. 3, in both the photographs W3, W4 in which the visible images of the right and left breasts 12, 14 are formed, the densities of the upper half portions where the chest wall portions K1, K2 do not exist are thick. Therefore, the photographs W3, W4 are butted against each other on the schaukasten so that the chest walls K1, K2 of the breasts are opposed to each other as shown in the lower left side of FIG. 3. In this case, the right and left photographs have the same density pattern, and the density patterns of the right and left images are identical to each other. Consequently, there is no difficulty in a diagnosis by the doctor.

As described above, in the mode where each of the chest wall portions K1, K2 of the breasts 12, 14 is recorded along the end portion of the thermal development recording material film FM which is parallel to the transportation direction, the image processing section 204 conducts the rotation process so that the breasts 12, 14 of the right and left mammo image data Q1, Q2 are directed in the same direction on the thermal development recording material film FM. Even in the state where the chest wall portions K1, K2 are butted against each other, therefore, the right and left mammo images can be easily compared with each other.

The invention is not restricted to the above-described embodiments, and may be variously modified or applied without departing from the spirit and scope of the invention.

For example, the image processing section 108 in the CR apparatus may not intentionally conduct the 180-degree rotation process of a mammo image, and the same result may be obtained. In this case, however, the image processing section 204 disposed in the thermal development apparatus must determine the necessity of the 180-degree rotation process. This determination can be conducted by referring a command which is supplied from the CR apparatus, and which indicates the presence or absence of the 180-degree rotation process, or by determining the directions of the breasts by means of image recognition.

In the embodiment of FIG. 2, the mammo image data Q2 is rotated. Alternatively, when, in the embodiment of FIG. 2, the breast in the mammo image data Q1 supplied from the CR apparatus 100 to the thermal development apparatus 200 is rightward directed and that in the mammo image data Q2 is leftward directed, for example, the image processing section 204 may rotate the mammo image data Q1 by 180 degrees.

In the embodiment of FIG. 3, the mammo image data Q2 is rotated. Alternatively, the mammo image data Q1 may be rotated in place of the mammo image data Q2.

What is claimed is:

1. A thermal development apparatus comprising:
    a transporting section that transports a thermal development recording material;
    an exposing section that exposes the thermal development recording material to form a latent image;
    an image processing section that applies a 180-degree rotation process on one of right and left breast image data, which are obtained by mammography, to be supplied to the exposing section, each of right and left images being formed on a sheet of the thermal development recording material.

2. The thermal development apparatus according to claim 1, wherein when the right and left breast images based on the right and left breast image data are to be formed in the thermal development recording material so that chest wall portions of the right and left breast images extend along an end portion which is in a direction perpendicular to a transportation direction of the thermal development recording material, the image processing section applies the rotation process so that each of the chest wall portions of the right and left breast images is formed at a record start position of the thermal development recording material.

3. The thermal development apparatus according to claim 1, wherein when right and left breast images based on the right and left breast image data are to be formed in the thermal development recording material so that chest wall portions of the right and left breast images extend along an end portion which is parallel to a transportation direction of the thermal development recording material, the image processing section applies the rotation process so that each of the chest wall portions of the right and left breast images is formed so as to be directed in a same direction on the thermal development recording material.

4. The thermal development apparatus according to claim 1, wherein the thermal development apparatus further comprises:
    a communication interface;
    a controlling section that controls collectively the operation of each section;
    a heater for a thermal development process;
    a heating controlling section that controls the heating operation of the heater;
    a film transportation controlling section that controls the transportation of the thermal development recording material film;
    a pair of film transportation roller; and
    a tip end detection sensor that detects the tip end of the film.

5. A medical system comprising: a radiographic imaging apparatus; and a thermal development apparatus connected to the radiographic imaging apparatus via a network, wherein the thermal development apparatus comprises:
    a transporting section that transports a thermal development recording material;
    an exposing section that exposes the thermal development recording material to form a latent image;
    an image processing section that applies a 180-degree rotation process on one of right and left breast image data, which are obtained by mammography, to be supplied to the exposing section, each of right and left images being formed on a sheet of the thermal development recording material.

6. The medical system according to claim 5, wherein when right and left breast images based on the right and left breast image data are to be formed in the thermal development recording material so that chest wall portions of the right and left breast images extend along an end portion which is in a direction perpendicular to a transportation direction of the thermal development recording material, the image processing section applies the rotation process so that each of the chest wall portions of the right and left breast images is formed at a record start position of the thermal development recording material.

7. The medical system according to claim 5, wherein when right and left breast images based on the right and left breast image data are to be formed in the thermal development recording material so that chest wall portions of the right and left breast images extend along an end portion which is parallel to a transportation direction of the thermal development recording material, the image processing section applies the rotation process so that each of the chest wall portions of the right and left breast images is formed so as to be directed in a same direction on the thermal development recording material.

8. The medical system according to claim 5, wherein the thermal development apparatus further comprises:
    a communication interface;
    a controlling section that controls collectively the operation of each section;
    a heater for a thermal development process;
    a heating controlling section that controls the heating operation of the heater;
    a film transportation controlling section that controls the transportation of the thermal development recording material film;
    a pair of film transportation roller; and
    a tip end detection sensor that detects the tip end of the film.

9. The medical system according to claim 5, wherein the radiographic imaging apparatus comprises:
    an X-ray source;
    X-ray acquisition unit;
    a mammo image data producing section that converts an image obtained from the X-ray acquisition unit to a mammo image data;
    an image processing section that applies a 180-degree rotation process on the produced mammo image data; and
    a communication interface.

10. The medical system according to claim 9, wherein the image processing section of the thermal development apparatus controls the 180-degree rotation process in the radiographic imaging apparatus.

11. The medical system according to claim 10, wherein the image processing section of the thermal development apparatus determines whether the rotation process in the thermal development apparatus is applied.

12. The medical system according to claim 5, wherein the radiographic imaging apparatus is a CR apparatus.

13. A thermal development method using the thermal development device according to claim 1, the method comprising:
    transporting a thermal development recording material;
    applying a 180-degree rotation process on one of right and left breast image data which are obtained by mammography, and which are to be supplied to the exposing section; and
    exposing the thermal development recording material to form a latent image.

14. The thermal development method according to claim 13, wherein when right and left breast images based on the right and left breast image data are to be formed in the thermal development recording material so that chest wall portions of the right and left breast images extend along an end portion which is in a direction perpendicular to a transportation direction of the thermal development recording material, the image processing section applies the rotation process so that each of the chest wall portions of the right and left breast images is formed at a record start position of the thermal development recording material.

15. The thermal development method according to claim 13, wherein when right and left breast images based on the right and left breast image data are to be formed in the thermal development recording material so that chest wall portions of the right and left breast images extend along an end portion which is parallel to a transportation direction of the thermal development recording material, the image processing section applies the rotation process so that each of the chest wall portions of the right and left breast images is formed so as to be directed in a same direction on the thermal development recording material.

* * * * *